United States Patent [19]
Bertram

[11] Patent Number: 5,285,776
[45] Date of Patent: Feb. 15, 1994

[54] ADAPTOR WITH TRACHEAL TUBE

[76] Inventor: Volker Bertram, Robert-Bosch-Str. 7, 7247 Sulz a.N., Fed. Rep. of Germany

[21] Appl. No.: 819,289

[22] Filed: Jan. 13, 1992

[30] Foreign Application Priority Data

Jan. 14, 1991 [DE] Fed. Rep. of Germany ....... 4100837

[51] Int. Cl.[5] ........................................... A61M 25/00
[52] U.S. Cl. ............................. 128/207.14; 128/912; 128/200.24; 285/319; 609/283; 609/905
[58] Field of Search .................. 128/207.14, 911, 912, 128/200.24, 202.27, DIG. 26; 285/319, 81, 340; 604/283, 905

[56] References Cited

U.S. PATENT DOCUMENTS

| | | | |
|---|---|---|---|
| 4,123,091 | 10/1978 | Cosentino | 285/39 |
| 4,673,199 | 6/1987 | Renfrew | 285/316 |
| 4,738,474 | 4/1988 | Jacob | 285/7 |
| 4,820,280 | 4/1989 | Berch | 604/248 |
| 4,852,563 | 8/1989 | Gross | 128/202.27 |
| 4,991,627 | 2/1991 | Nix | 137/614.03 |
| 5,052,386 | 10/1991 | Fischer | 128/207.15 |
| 5,106,127 | 4/1992 | Briet | 285/4 |
| 5,131,691 | 7/1992 | Washizu | 285/319 |

FOREIGN PATENT DOCUMENTS

| | | | |
|---|---|---|---|
| 406584 | 1/1991 | European Pat. Off. | 128/912 |
| 2635871 | 2/1978 | Fed. Rep. of Germany | 285/319 |
| 663539 | 12/1951 | United Kingdom . | |
| 718411 | 11/1954 | United Kingdom . | |
| 1042774 | 9/1966 | United Kingdom | 285/319 |
| 1457892 | 12/1976 | United Kingdom . | |
| 2049087 | 12/1980 | United Kingdom . | |
| 2199630 | 7/1988 | United Kingdom . | |

*Primary Examiner*—Edgar S. Burr
*Assistant Examiner*—Eric P. Raciti
*Attorney, Agent, or Firm*—Michael J. Striker

[57] ABSTRACT

An assembly has a tracheal tube and an adaptor having a connecting tube insertable in the tracheal tube and a connecting piece connectable with a resuscitation tube. The adaptor has at least one clamping member adapted to press a part of the tracheal tube located on the connecting tube from outside and yielding during mounting the tracheal tube so as to secure the tracheal tube against removal from the connecting tube. The clamping member is formed so that prior to pushing of the tracheal tube onto the connecting tube the clamping member has a smaller radial spacing from the connecting tube than a wall thickness of the tracheal tube.

3 Claims, 3 Drawing Sheets

ADAPTOR WITH TRACHEAL TUBE

BACKGROUND OF THE INVENTION

The present invention relates to an adaptor with a tracheal tube.

More particularly, the present invention relates to an adaptor with tracheal tube, which has a connecting tube insertable in the tracheal tube and the connecting piece connectable to a resuscitation tube.

For the resuscitation of patients endotracheal tubes are connected via an adaptor to the resuscitation tubes leading to resuscitors or respirators. Therefore the adaptors form the connecting piece between an individual adapted endotracheal tube and the resuscitation tubes. As a function of the patient, the internal diameter of the endotracheal tubes can vary between 2 and 10 mm. There is often also a need of not only adapting the endotracheal tube diameter to the patient, but also its length. Thus, prior to intubation, the treating doctor or surgeon often has to cut the endotracheal tube to a desired length and then connect it to the adaptor.

Adaptors are known having a connecting tube on which the endotracheal tube is engaged. This connecting tube passes into a connecting piece to which the resuscitation tubes are connected. The connecting piece generally has an internal diameter of at least 10 mm. The connecting tube can have a conical outer wall, which passes in a very flat or shallow manner towards the mouth. On pushing on the endotracheal tube, the latter widens in accordance with the conical configuration of the connecting tube. This is intended to provide a good grip of the endotracheal tube on the connecting tube. However, disconnection problems occur with these known adaptors. As a result of saliva and the heat present in the oral cavity, the already soft material endotracheal tube becomes so soft that it can be detached from the adaptor connecting tube. It is therefore necessary to constantly check the correct seating of the endotracheal tube, because otherwise there is a risk of disconnection between the tube and the adaptor.

SUMMARY OF THE INVENTION

The object of the invention is to develop an adaptor, so that a tracheal tube fitted by pushing on to the adaptor connecting tube is reliably connected to the adaptor.

In keeping with these objects and with others which will become apparent hereinafter, one feature of the present invention resides, briefly stated in an adaptor with a tracheal tube, in which at least one clamping member presses on a part of the tracheal tube located on the connecting tube and yields on mounting the tracheal tube, and the clamping member secures the tracheal tube in self-locking or automatically interlocking manner against removal from the connecting tube, and the structure is designed so that prior to pushing on of the tracheal tube, the clamping member has a smaller radial spacing from the connecting tube than the wall thickness of the tracheal tube.

Through the use of at least one self-locking clamping member, which engages on the casing of the tracheal tube, a reliable connection between the tracheal tube and the adaptor is produced. On pushing on the tracheal tube the clamping member moves radially backwards, whereas on attempting to pull off the tracheal tube the clamping member or members engage in the tracheal tube wall.

Preferably the clamping members are in the form of clamping tongues directed at an acute angle inwards against the connecting tube and which on a clamping ring project inwards in spoke-like manner. Such a clamping ring can easily be produced as a plastic injection moulding with an extremely small material expenditure. The adaptor and the clamping ring can be made from the same plastics material.

The clamping ring can be particularly easily axially pushed over the connecting tube and connected to the adaptor, if interengaging locking elements are constructed on the adaptor and the clamping ring. Thus, an adaptor pipe can be provided with a circular groove, in which engages a socket of the clamping ring with a locking ring. The clamping members of the clamping ring are arranged in such a way that at their tips they have a smaller spacing from the adaptor connecting tube than the tracheal tube wall thickness. As a result the locking members are always in engagement with the tracheal tube wall and secure same in self-locking or automatically locking manner against removal from the connecting tube.

From its projecting end, the connecting tube can have a conically widening external diameter. The connecting tube also can be formed in such a way that the outer wall is initially straight and only then passes into a conical configuration. The straight portion of the connecting tube can be very accurately adapted to the internal diameter of the tracheal tube to be connected and it is ensured that the tracheal tube can be very easily pushed over the straight portion without widening.

The transition from the connecting tube to the connecting piece for the resuscitation tubes preferably takes place by means of a funnel-shaped widening of the connecting tube, which terminates at the opening edge of the connecting piece. This means that the internal diameter of the connecting piece tapers directly from the opening in funnel-shaped manner to the connecting tube within the connecting piece. This prevents undesired "dead spaces", so that optimum resuscitation or respiration is possible.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
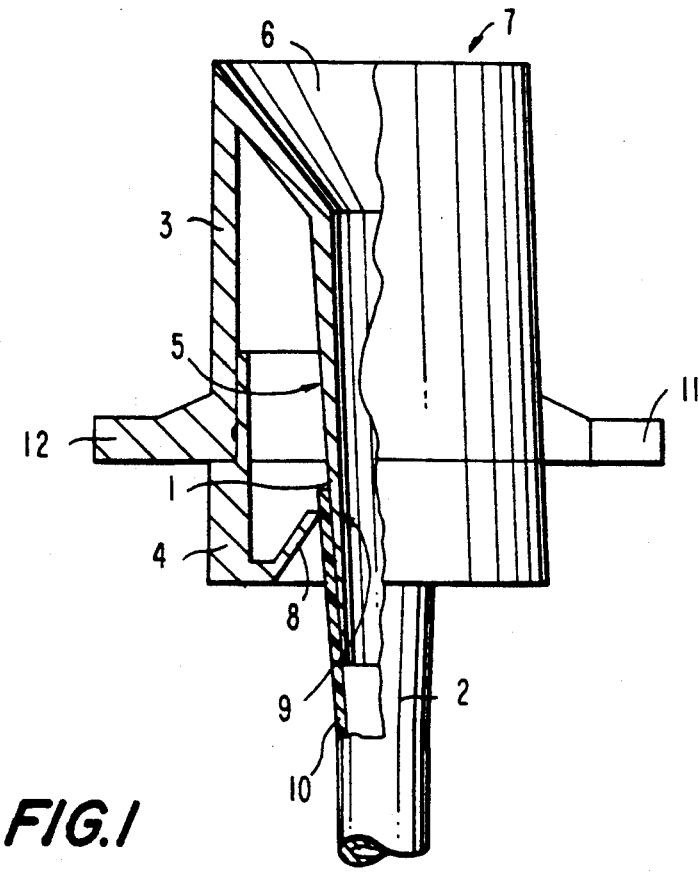
FIG. 1 An inventive adaptor with a fitted tracheal tube.

The adaptor shown in FIG. 1 comprises a connecting tube 1, onto which is pushed a tracheal tube 2. The connecting tube 1 has a connecting piece 3 for fitting the here not shown resuscitation tubes and a clamping ring 4. The connecting tube 1 has a conically widening outer wall and passes in the form of a funnel 6 to the diameter of the connecting piece 3. The funnel opening 7 simultaneously forms the connecting opening of the connecting piece 3.

The clamping ring 4 has inwardly directed clamping tongues 8, which engage with their tip 9 in the wall 10 of the tracheal tube 2.

Figure 4:
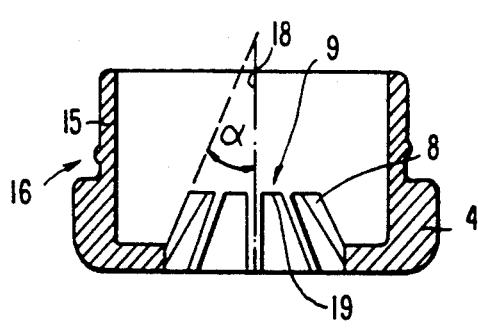
FIG. 4 The cross-section through a clamping ring.
Figure 5:
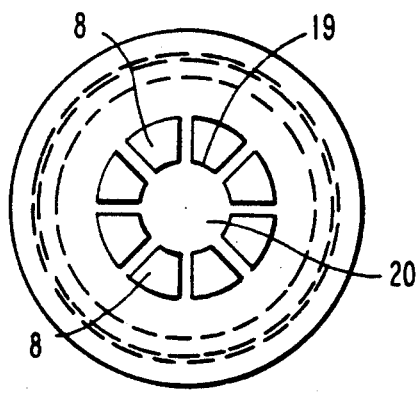
FIG. 5 The front view of the clamping ring of FIG. 4.

The construction of the clamping rings 4 is made clearer in FIGS. 4 and 5. Two fastening tongues 11, 12 project laterally from the adaptor, and a fastening band can be fixed to them in the conventional manner.

Figure 2:
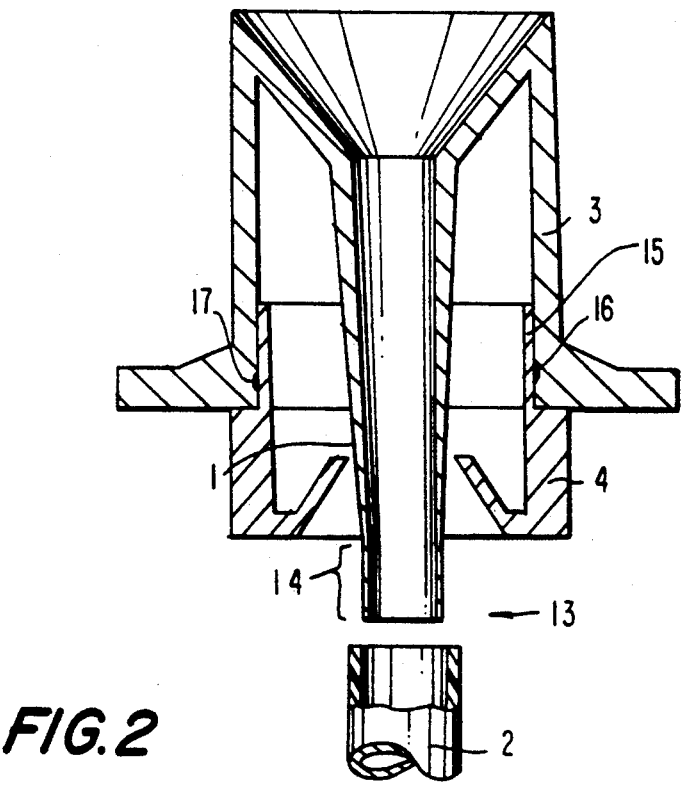
FIG. 2 An adaptor with a partly straight connecting tube for the tracheal tube.

FIG. 2 shows an adaptor, construction in cross-section. The connecting tube of the adapter has a projecting end 13 with straight tube portion 14, which then passes into a conical tube portion. The external diameter of the straight tube portion 14 can be accurately adapted to the internal diameter of the not widened tracheal tube 2.

As in the embodiment according to FIG. 1, the clamping ring 4 is engaged on the adaptor in such a way that a socket 15 shaped on to the clamping ring 4 engages in the connecting piece 3. Onto the socket 15 is shaped an all-round locking ring 16, which engages in a corresponding circular groove 17 of the connecting piece 3.

Figure 3:
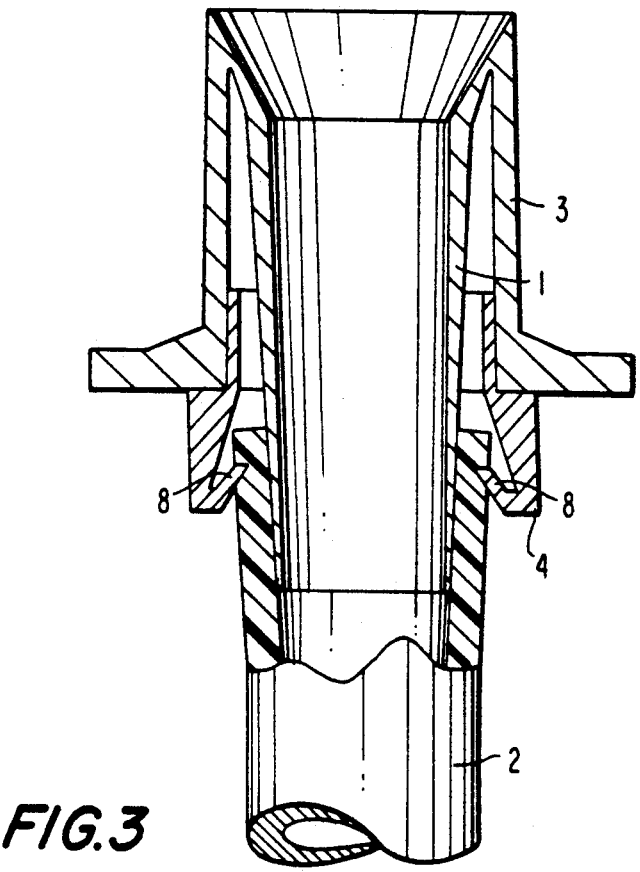
FIG. 3 An adaptor with tracheal tube having a large internal diameter.

FIG. 3 shows a construction with a much larger connecting tube diameter. However, the function of the individual elements corresponds entirely to those of FIGS. 1 and 2.

The clamping ring 4 shown in FIG. 4 has several inwardly directed clamping members 8, which are at an acute inclination angle to the central axis 18. The clamping members 8 are constructed as radially elastically resilient clamping tongues. The tips 9 of the clamping tongues form narrow, tapering locking edges 19, which segmentally surround an annular space 20 as shown in FIG. 5. As can be gathered from FIG. 1 to 3, the connecting tube 1 projects through the annular space 20. The shaped locking ring 16 passes round the socket 15.

The adaptor, including the mounted clamping ring 4, is preferably made from plastic and the clamping ring 4 can be made from a plastics material giving the clamping members 8 the necessary elasticity and stability.

Figure 6:
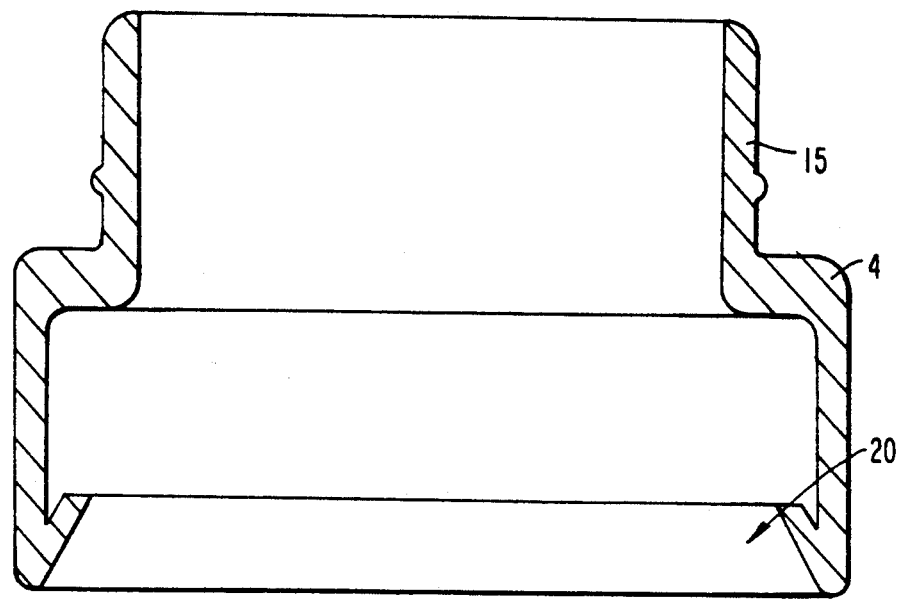
FIG. 6 A cross-section through a clamping ring for very large diameter tracheal tubes.

FIG. 6 is a much larger scale representation of a clamping ring 4 for particularly large tracheal tubes.

The diameter of the annular space 20 is here larger than the internal diameter of the socket 15.

Figure 7:
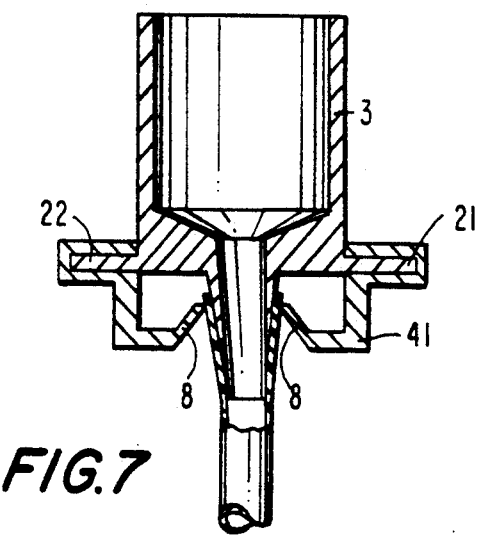
FIG. 7 Another construction with a rectangular clamping part mounted on the connecting piece and in cross-section.
Figure 9:
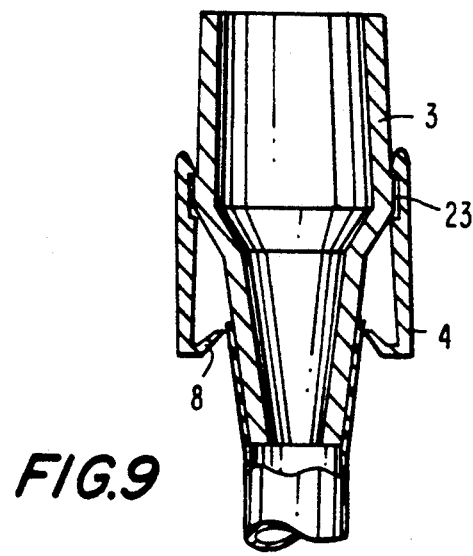
FIG. 9 Another embodiment with a clamping ring engaging over the connecting piece in cross-section.
Figure 8:
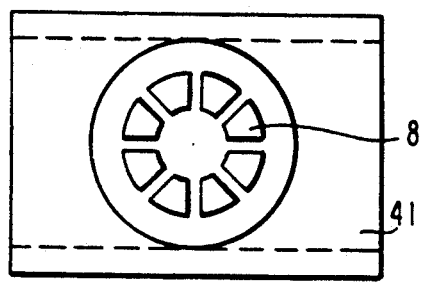
FIG. 8 A front view of the clamping part of FIG. 7.
Figure 10:
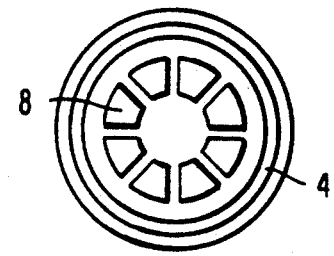
FIG. 10 The front view of the clamping ring of FIG. 9.

FIGS. 7 to 10 show further embodiments, in which the embodiment of FIG. 7 has a rectangular clamping part 41, which engages over the connecting piece 3 at tongues 21, 22. The clamping ring 4 of FIG. 10 engages over the connecting piece 3 on a rim 23 passing round in circular manner.

It will be understood that each of the elements described above, or two or more together, may also find a useful application in other types of constructions differing from the types described above.

While the invention has been illustrated and described as embodied in an adaptor for tracheal tube, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. An assembly, comprising a tracheal tube having a wall thickness; and an adaptor having a connecting tube insertable in said tracheal tube and a connecting piece connectable with a resuscitation tube, said connecting tube having a free end which faces said tracheal tube and at least two tube portions including a first tube portion which extends from said free end and is straight and a second tube portion which is axially spaced from and which extends axially from said first tube portion and is conically widening away from said first tube portion, said adaptor having at least one clamping member including a ring provided with several clamping tongues directed at an acute angle inwards and pressing a portion of said tracheal tube located on said connecting tube from outside and yielding during mounting said tracheal tube so as to secure said tracheal tube against removal from said connecting tube, said clamping member being formed so that prior to pushing of said tracheal tube onto said connecting tube said clamping member has a similar radial spacing from said connecting tube than said wall thickness of said tracheal tube.

2. An assembly as defined in claim 1, wherein said adaptor has an annular space through which said connecting tube projects, said clamping members segmentally surrounding said annular space.

3. An assembly as defined in claim 1, wherein said connecting piece has an opening, said connecting tube located inside said connecting piece having a funnel-shaped portion with a funnel opening which forms said opening of said connecting piece.

* * * * *